United States Patent [19]
Haugland et al.

[11] Patent Number: 5,248,782

[45] Date of Patent: Sep. 28, 1993

[54] LONG WAVELENGTH HETEROARYL-SUBSTITUTED DIPYRROMETHENEBORON DIFLUORIDE DYES

[75] Inventors: Richard P. Haugland; Hee C. Kang, both of Eugene, Oreg.

[73] Assignee: Molecular Probes, Inc., Eugene, Oreg.

[21] Appl. No.: 629,596

[22] Filed: Dec. 18, 1990

[51] Int. Cl.$^5$ .............. C07D 209/56; C07D 209/00; H01S 3/213

[52] U.S. Cl. ........................... 548/110; 252/301.7; 372/39; 372/53; 372/54; 548/405; 544/229

[58] Field of Search ............... 548/110, 405; 544/229

[56] References Cited

U.S. PATENT DOCUMENTS

| | | | |
|---|---|---|---|
| 3,733,334 | 5/1973 | Padmanathan I | 548/110 |
| 3,769,300 | 10/1973 | Padmanathan II | 548/405 |
| 4,774,339 | 9/1988 | Haugland et al. | 548/405 |
| 4,839,260 | 6/1989 | Logan I | 548/110 X |
| 4,839,274 | 6/1989 | Logan II | 548/110 X |
| 4,916,711 | 4/1990 | Boyer et al. | 372/53 |

OTHER PUBLICATIONS

Falk et al., Monatshefte Fur Chemie, vol. 110, pp. 987 to 1001 (1979).
Treibs & Kreuzer et al I, *Difluorboryl-komplexe von di-und tripyrrylmethenen*, Liebigs Annalen Chem. 718, 208-223 (1968).
Wories, et al., *A novel water-soluble fluorescent probe; Synthesis, luminescence and biological properties of the sodium salt of the 4-sulfonato-3,3',5,5'-tetramethyl-2,2'-pyrromethen-1,1'-BF$_2$complex*, Recl. Trav. Chim. Pays-Bas 104, 288-291 (1985).
Pavlopoulos, et al., *Laser action from a tetramethylpyrromethene-BF$_2$ complex*, App. Optics 27, 4998-4999 (1988).
Demas & Crosby, J. Phys. Chem. 75, 991-1024 (1971).
H. Rapoport et al., J. Am. Chem. Soc. 84, 2178-2181 (1962).
R. M. Silverstein et al., Org. Synth. Coll. vol. IV, pp. 831-833 (1970).
A. Treibs et al., II Ann. Der Chemie 739, 225-227 (1970).
C. F. H. Allen et al., Org. Synth. Coll. vol. III, pp. 358-360 (1960).
J. A. S. Cavaleiro, et al., J. Org. Chem. 53, 5847-5849 (1988).
C. G. Kruse, et al. Heterocycles 26, 3141-3151 (1987).

*Primary Examiner*—Floyd D. Higel
*Attorney, Agent, or Firm*—Allegra J. Helfenstein

[57] ABSTRACT

This invention describes novel 4,4-difluoro-4-bora-3a,-4a-diaza-s-indacenes containing heteroaryl substituents conjugated to the fluorophore and methods for their synthesis. The heteroaryl substituted compounds (heteroaryl dyes) generally have the structure:

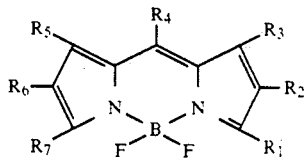

wherein any or all of the substituents $R_1$-$R_7$, but at least one of such substituents, is a heteroaryl group, including 5- or 6-member rings, singly or fused, containing one or more heteroatoms. The new dyes that have spectral properties that are significantly shifted from those of the parent alkyl-substituted dyes, usually accompanied by an increase in photostability and in some cases by an increase in the extinction coefficient relative to the alkyl-substituted dyes. The general method of synthesis includes formation of pyrromethene salt intermediates followed by cyclization with boron trifluoride in the presence of a base to give heteroaryl-substituted dipyrrometheneboron difluoride dyes.

20 Claims, 5 Drawing Sheets

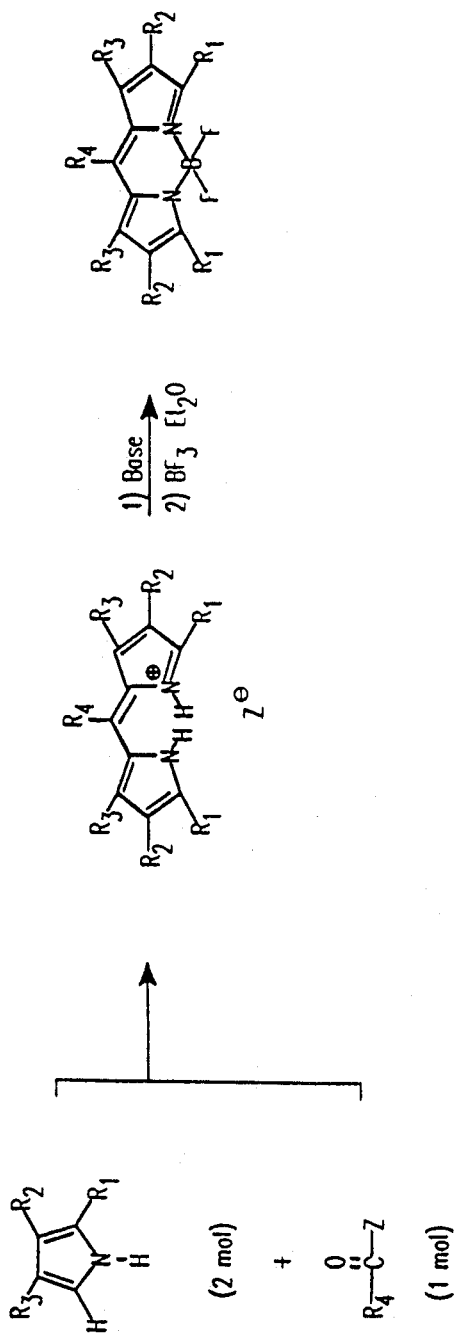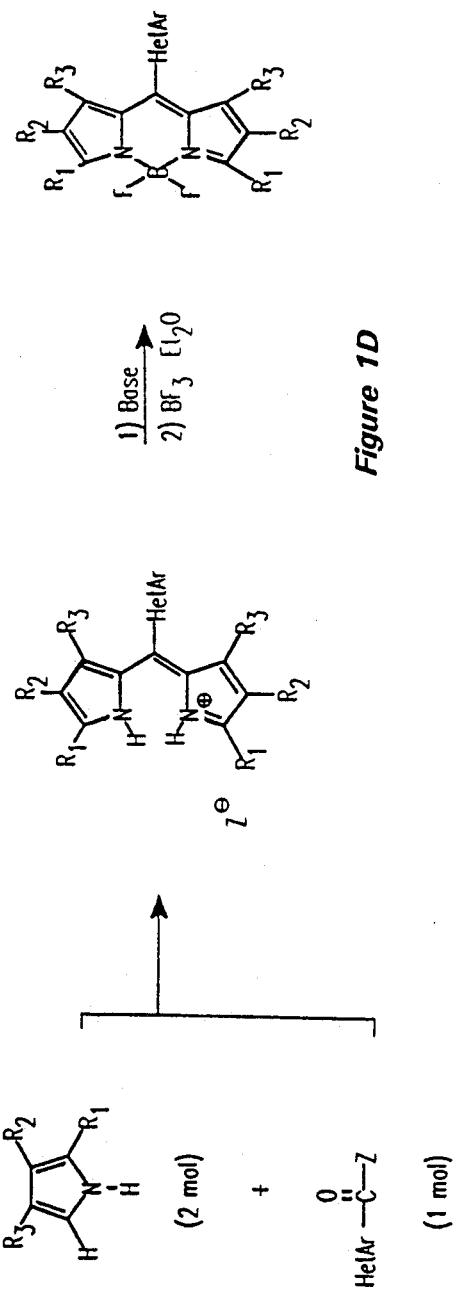
Figure 1C
Figure 1D

LONG WAVELENGTH HETEROARYL-SUBSTITUTED DIPYRROMETHENEBORON DIFLUORIDE DYES

FIELD OF THE INVENTION

This invention relates to improvements in fluorescent dyes, particularly to dyes that are heteroaryl-substituted derivatives of dipyrrometheneboron difluoride dyes (derivatives of 4,4-difluoro-4-bora-3a,4a-diaza-s-indacene dyes) that absorb light at wavelength longer than 500 nm. These dyes have certain advantages over other dyes that absorb at these wavelengths of being electrically neutral, photostable and being, in most cases, highly fluorescent with relatively narrow absorption and emission spectra.

BACKGROUND OF THE INVENTION

Fluorescent dyes have many uses and are known to be particularly suitable for biological applications in which the high detectability of fluorescence is required. Examples of their utility include use in immunoassays, labeling nucleotides and oligonucleotides for hybridization studies, binding to polymeric microspheres and staining of cells for use in imaging studies. Dyes are also used for selective destruction of cells such as in the technique of photodynamic therapy.

Fluorescence useful for such applications is generally initiated by absorption of light from an external, relatively concentrated light source. The sensitivity of these applications is improved by having dyes that have high absorbance of the exciting light and high fluorescence quantum yield. The applications are furthermore improved by having dyes that resist photobleaching by the exciting light and that have spectral wavelengths in a range that avoids the background from contaminants that may be present in the samples. For many biological applications it is useful to have dyes whose fluorescence is not quenched by water, since most biological measurements are made in aqueous solution.

Certain lasers are particularly useful as a concentrated light source for the excitation of fluorescence. These include the argon laser with principal output at 488 nm and 514 nm; helium-neon lasers that can be selected to have maximum output at either 543 nm, 594 nm, or 633 nm; the krypton laser which has significant output at 568 nm and 647 nm; and light emitting diodes, which are commonly available at this time, with output above 660 nm.

A number of dyes have previously been found to be fluorescent, however many of these dyes have characteristics which interfere with their usefulness. For example, many known fluorescent dyes do not have significant absorbance at the desired excitation wavelengths, or are significantly quenched in aqueous solution or are unstable during the illumination.

Dyes derived from dipyrrometheneboron difluoride have many desirable characteristics. Simple alkyl derivatives of the fluorophore 4,4-difluoro-4-bora-3a,4a-diaza-s-indacene have been described by Treibs & Kreuzer, *Difluorboryl-komplexe von di- und tripyrrylmethenen*, LIEBIGS ANNALEN CHEM. 718, 203 (1968) and by Worries, Kopek, Lodder, & Lugtenburg, *A novel water-soluble fluorescent probe: Synthesis, luminescence and biological properties of the sodium salt of the 4-sulfonato-3,3',5,5'-tetramethyl-2,2'-pyrromethen-1,1'-BF₂complex*, RECL. TRAV. CHIM. PAYS-BAS 104, 288 (1985) as being highly fluorescent with spectral properties that are similar to fluorescein with maximum absorbance at about 490 to 510 nm and maximum emission at about 500 to 530 nm. U.S. Pat. No. 4,774,339 to Haugland et al. (1988) ('339 patent) describes 4,4-difluoro-4-bora-3a,4a-diaza-s-indacene (dipyrrometheneboron difluoride) dyes including aryl-substituted derivatives that contain reactive groups suitable for conjugation to biomolecules, that have good photostability, and which have fluorescein-like spectra. Neither the earlier references nor the '339 patent does not disclose the subject heteroaryl dyes or enhanced long wavelength fluorescence properties of their dyes.

As described in the '339 patent, and by Pavlopoulos, et al., *Laser action from a tetramethylpyrromethene-BF₂ complex*, APP. OPTICS 27, 4998 (1988), the emission of the alkyl derivatives of 4,4-difluoro-4-bora-3a,4a-diaza-s-indacene fluorescent dyes clearly overlaps that of fluorescein. The overlap allows the alkyl derivatives of dipyrrometheneboron difluoride to be used with the same optical equipment as used with fluorescein-based dyes without modification of the excitation sources or optical filters. As a result of the same spectral characteristics, however, the fluorescence of the known class of alkyl-substituted 4,4-difluoro-4-bora-3a, 4a-diaza-s-indacenes is not readily suitable for detection in combination with fluorescein or for use in applications where excitation by longer wavelength sources such as the helium-neon or krypton lasers or light emitting diodes is required.

Heteroaryl-substituted dipyrrometheneboron difluoride dyes described in this invention have significant absorbance and fluorescence at desired wavelengths, high fluorescence in aqueous solution and good photostability and are thus particularly useful as fluorescent dyes. Furthermore, the subject fluorescent dyes are desirable for use in combination with other fluorescent dyes such as fluorescein or alkyl-substituted 4,4-difluoro-4-bora-3a,4a-diaza-s-indacene dyes in that their fluorescence can be selectively determined by their spectral shift to longer wavelengths, particularly their emission at greater than 540 nm. There are no previously reported examples of 4,4-difluoro-4-bora-3a,4a-diaza-s-indacene dyes that contain heteroaryl-substituents or that have been described that have such long wavelength spectral properties.

SUMMARY OF THE INVENTION

This invention describes novel 4,4-difluoro-4-bora-3a,4a-diaza-s-indacenes containing heteroaryl substituents conjugated to the fluorophore ("heteroaryl dyes") and methods for their synthesis. A heteroaryl group is an aromatic group that contains at least one heteroatom (a non-carbon atom forming the ring structure). A ring can be a 5- or 6-member ring. The heteroaryl group can be a single ring structure or a fused two-ring structure. The heteroaryl group can contain one or more heteroatoms.

Incorporation of heteroaryl substituents results in new dyes that have spectral properties that are significantly shifted from those of the parent alkyl-substituted fluorophore, thus permitting their use in multi-color fluorescence applications in combination with fluorescein or alkyl-substituted 4,4-difluoro-4-bora-3a,4a-diaza-s-indacenes. Furthermore, this wavelength shift is usually accompanied by an increase in photostability of the heteroaryl dyes and in some cases by an increase in the extinction coefficient of the heteroaryl dyes relative to the alkyl-substituted 4,4-difluoro-4-bora-3a,4a-diaza-s-indacenes.

In general, there are two synthetic routes to the heteroaryl dyes depending on whether the dyes are symmetric or asymmetric, and each of these two routes has two variations, as generally described in FIG. 1.

DESCRIPTION OF THE DRAWINGS

FIG. 1 is a general reaction scheme for synthesis of heteroaryl dyes. The general method consists of a formation of pyrromethene intermediates followed by cyclization with boron trifluoride in the presence of base to give heteroaryl-substituted dipyrrometheneboron difluoride dyes.

FIG. 1C gives a synthetic method of symmetric heteroaryl dyes that contain two heteroaryl substituents. Condensation of a heteroaryl pyrrole having hydrogen atom at the 2-position and a reactive carbonyl derivative yields a symmetric pyrromethene intermediate, which is further converted to a final product with boron trifluoride in the presence of a base. FIG. 1D shows a synthetic method of symmetric dyes that contain a heteroaryl substituent at the 8-position of the dyes. The heteroaryl group is introduced into the mesoposition of a pyrromethene intermediate by the use of an appropriate heteroary carbonyl derivative.

DETAILED DESCRIPTION OF THE EMBODIMENTS

Figure 1A:
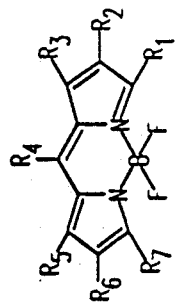
FIG. 1A shows a method of synthesis of asymmetric heteroaryl dyes. Condensation of a heteroaryl-substituted pyrrole and a second pyrrole derivative having an aldehyde or ketone function at the 2-position, with an acid yields a pyrromethene intermediate. This pyrromethene intermediate is converted to a heteroaryl dye with boron trifluoride in the presence of base.
Figure 1A:
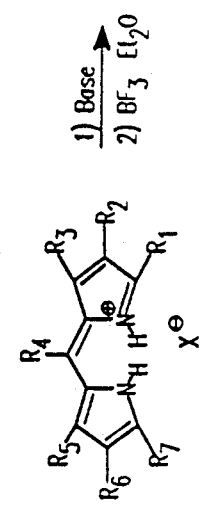
Figure 1A:
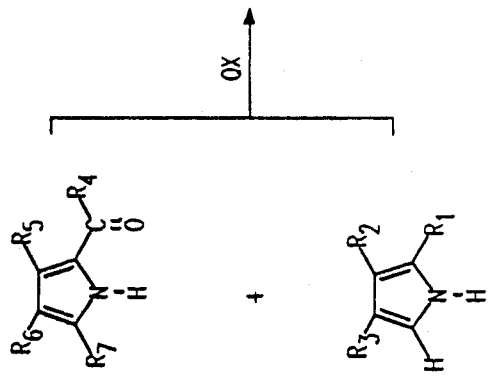
Figure 1B:
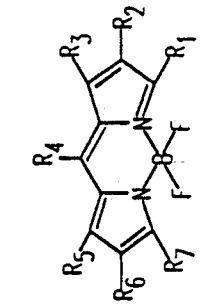
FIG. 1B also shows a synthetic scheme for asymmetric heteroaryl dyes. In this method, the heteroaryl-substituted pyrrole contains the required aldehyde or ketone function which provides methene bridge of the pyrromethene intermediate.
Figure 1B:
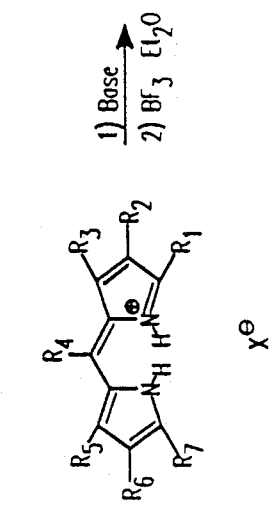
Figure 1B:
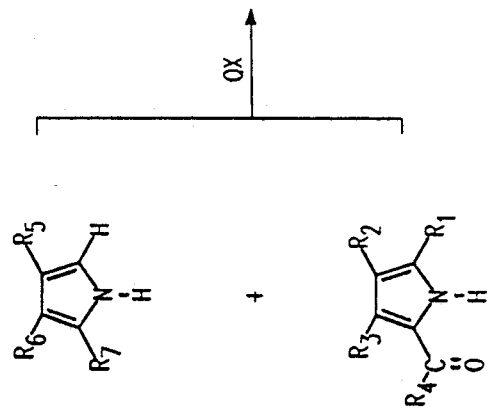

This invention describes novel heteroaryl-substituted 4,4-difluoro-4-bora-3a,4a -diaza-s-indacene dyes and methods for their synthesis. The heteroaryl-substituted compounds (heteroaryl dyes) generally have the structure:

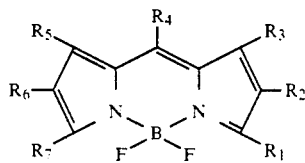

wherein any or all of the substituents $R_1$–$R_7$, but at least one of such substituents, is a heteroaryl group. Typically, because of the symmetry, at least one of the groups $R_1$, $R_2$, $R_3$ or $R_4$ is a heteroaryl group. Multiple heteroaryl substituents, in combinations of $R_1$–$R_7$, may be the same or different. In one embodiment of the invention, at least two of the substituents $R_1$–$R_7$, which may be the same or different, are heteroaryl residues. Generally, substituents that are not heteroaryl groups include hydrogen, halogen, alkyl, cycloalkyl, aryl, arylalkyl, acyl, or sulfo, alone or in combination.

In one embodiment of the invention, the heteroaryl group is a single ring structure containing one or more heteroatoms, for example, the heteroaryl substituent is pyrrole, thiophene, or furan (single ring, single heteroatom), or oxazole, isoxazole, oxadiazole, or imidazole (single ring, multiple heteroatoms). Alternatively, the heteroaryl group is a multiring structure containing one or more heteroatoms, for example, the heteroaryl substituent is benzoxazole, benzothiazole, or benzimidazole, (multi-ring, multiple heteroatoms), or benzofuran or indole (multi-ring, single heteroatom). The invention includes both heteroaryl substituents and substituted derivatives of the heteroaryl substituents, such as the preferred heteroaryl dyes where $R_1$ is pyrrolyl; or alkyl-, aryl-, arylalkyl- or heteroaryl-substituted pyrrolyl. In other preferred heteroaryl dyes, $R_1$ is thienyl; or alkyl-, aryl-, arylalkyl- or heteroaryl-substituted thienyl. In additional preferred embodiments of the heteroaryl dyes, $R_1$ and $R_7$, which may be the same or different, are pyrrolyl; or alkyl-, aryl-, arylalkyl- or heteroaryl-substituted pyrrolyl. Alternatively, $R_1$ and $R_7$, which may be the same or different, are thienyl; or alkyl-, aryl-, arylalkyl- or heteroaryl-substituted thienyl. Table 1 contains a sample of representative heteroaryl dyes.

TABLE 1

EXAMPLES OF NEW HETEROARYL-SUBSTITUTED DIPYRROMETHENEBORON DIFLUORIDE DYES

| COMPOUND | $R_1$ | $R_2$ | $R_3$ | $R_4$ | $R_5$ | $R_6$ | $R_7$ |
|---|---|---|---|---|---|---|---|
| 1 | PYR | H | H | H | $CH_3$ | H | $CH_3$ |
| 2 | PYR | H | H | H | Ph | H | Ph |
| 3 | OXZ | H | H | H | $CH_3$ | H | $CH_3$ |
| 4 | OXZ | H | H | H | Ph | H | Ph |
| 5 | BOZ | H | H | H | Ph | H | Ph |
| 6 | $CH_3$ | H | $CH_3$ | IMD | $CH_3$ | H | $CH_3$ |
| 7 | MBF | H | H | APh | H | H | MBF |
| 8 | THI | H | H | H | $CH_3$ | H | $CH_3$ |
| 9 | THI | H | H | H | Ph | H | Ph |
| 10 | THI | H | H | H | H | H | THI |
| 11 | THI | H | H | $CH_3$ | H | H | THI |
| S* | $CH_3$ | H | $CH_3$ | H | $CH_3$ | H | $CH_3$ |

*Compound S is included as a standard example of an alkyl-substituted dipyrrometheneboron difluoride dye, for comparison.

The examples are preferred, representative compounds only and are not intended to be exclusive.

The names and chemical structures of abbreviations used in this Table are shown immediately below.

PYR: Pyrrol-2-yl 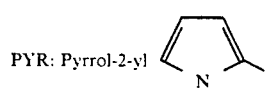

OXZ: Oxazol-5-yl 

BOZ: Benzoxazol-2-yl 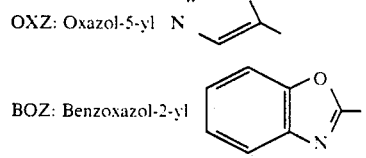

TABLE 1-continued

EXAMPLES OF NEW HETEROARYL-SUBSTITUTED DIPYRROMETHENEBORON DIFLUORIDE DYES

| COMPOUND | $R_1$ | $R_2$ | $R_3$ | $R_4$ | $R_5$ | $R_6$ | $R_7$ |
|---|---|---|---|---|---|---|---|

IMD: Imidazol-2-yl

MBF: 2-Methylbenzofuran-3-yl

APh: 2-Actoxyphenyl

THI: Thien-2-yl

In general, there are two synthetic routes to heteroaryl-substituted 4,4-difluoro-4-bora-3a,4a-diaza-s-indacene dyes depending on whether the dyes are symmetric or asymmetric (FIG. 1) and each of these two routes has two variations. Synthesis of heteroaryl-substituted 4,4-difluoro-4-bora-3a,4a-diaza-s-indacene dyes requires the preparation of suitable pyrrole precursors substituted only at the 2, 3 and/or 4 positions with at least one heteroaryl substituent.

In the asymmetric synthesis of heteroaryl-substituted 4,4-difluoro-4-bora-3a,4a-diaza-s-indacene dyes (FIG. 1A), this heteroaryl pyrrole derivative is condensed in a reaction mediated by a suitable acid QX with a second pyrrole derivative that contains an aldehyde or ketone function in the 2-position used in approximately stoichiometric proportions to yield an intermediate pyrromethene salt. Suitable acids QX include, but are not limited to, hydrogen halides, metal salts typically used in Friedel-Crafts reactions such as zinc halides and nonmetallic, electron deficient Lewis acids such boron halides, halides of sulfur acids and phosphorousoxychloride, that such acids contain elements or group of elements capable of forming an anionic counterion. Preferred is hydrogen bromide, since its use results in moderate to good yields of the heteroaryl-substituted pyrromethene salts. In some cases it may be practical to use boron trifluoride as both the acid component and to complete formation of the 4,4-difluoro-4-bora-3a,4a-diaza-s-indacene dye in a "one-pot reaction". Cyclization of the heterocyclic ring formation of the asymmetric 4,4-difluoro-4-bora-3a,4a-diaza-s-indacene dye is completed by addition of boron trifluoride in combination with a suitable base (e.g. EXAMPLES 1,2,4,5,8,9). Boron trifluoride is preferably used as one of its ether complexes because of the ease of handling these complexes rather than the gaseous reagent. Suitable bases include, but are not limited to trimethylamine, triethylamine, N,N-diisopropylethylamine, tetramethylethylenediamine, 1,8-bis(dimethylamino)naphthalene, diazabicyclooctane, and diazabicycloundecene, 4-dimethylaminopyridine and 4-pyrrolidinopyridine, and other similar strong bases.

In a variation of the asymmetric 4,4-difluoro-4-bora-3a,4a-diaza-s-indacene dye synthesis (FIG. 1B), the heteroaryl pyrrole can contain the required aldehyde or ketone substituent that is necessary to provide the methene bridge of the pyrromethene intermediate. This heteroaryl pyrrole aldehyde or ketone is condensed in a reaction mediated by a suitable acid QX, with approximately stoichiometric proportions of a second pyrrole derivative to give a heteroaryl-substituted pyrromethene salt (e.g. EXAMPLE 3).

Alternatively, to produce symmetric heteroaryl-substituted 4,4-difluoro-4-bora-3a,4a-diaza-s-indacene dyes that contain two heteroaryl residues (FIG. 1C), heteroaryl pyrrole derivatives that contain a hydrogen atom on the carbon in the 2 position are condensed with an aldehyde, an acid halide or a carbonyl derivative R—(C=O)—Z that has been activated to electrophilic aromatic substitution reactions by incorporation of a residue Z to increase the electron deficiency of the carbonyl group. The group —(C=O)—Z defines an ester, amide, imide, anhydride or acid halide. In the case of Z=H, the intermediate R—(C=O)—Z is an aldehyde. In this case it is found that the heteroaryl-substituted pyrromethene salt is still formed with the required oxidation coming from molecular oxygen or added oxidizing agents. The symmetric pyrromethane intermediate can be converted by a source of boron trifluoride in combination with a base to the symmetrically substituted 4,4-difluoro-4-bora-3a,4a-diaza-s-indacene dyes (e.g. EXAMPLE 10).

In a variation of the symmetric 4,4-difluoro-4-bora-3a,4a-diaza-s-indacene dye synthesis that contains a single heteroaryl substituent (FIG. 1D) the heteroaryl group is introduced into the 8 position of the 4,4-difluoro-4-bora-3a,4a-diaza-s-indacene dye by use of an appropriate heteroaryl acid halide, anhydride or heteroaryl aldehyde derivative in the place of the acid halide or anhydride component (e.g. EXAMPLES 6,7).

Several methods for synthesis of heteroaryl pyrrole precursors for heteroaryl-substituted 4,4-difluoro-4-bora-3a,4a-diaza-s-indacene dyes are given in Experimental Examples described below. The Examples serve to illustrate the generality of the methods and properties of the heteroaryl dyes. Among the heteroaryl substituents that are described in the Examples are oxazole (EXAMPLES 3,4), benzofuran (EXAMPLE 7), imidazole (EXAMPLE 6), benzoxazole (EXAMPLE 5), benzothiazole (EXAMPLE 11), benzimidazole (EXAMPLE 12), pyrrole (EXAMPLES 1,2) and thiophene (EXAMPLES 8,9,10). It will be obvious to one skilled in the art that synthesis of many other 4,4-difluoro-4-bora-3a,4a-diaza-s-indacene dyes that contain other heteroaryl substituents can be accomplished using other heteroaryl pyrrole precursors that contain substituents compatible with the chemistry in FIG. 1 and such heteroaryl-substituted 4,4-difluoro-4-bora-3a,4a-diaza-s-indacene dyes from other heteroaryl pyrrole precursors will fall within the description of the invention.

Once prepared, the heteroaryl-substituted 4,4-difluoro-4-bora-3a,4a-diaza-s-indacene dyes may be further modified by sulfonation, nitration, alkylation, acylation, halogenation and other reactions by methods known in the art, such as described by Worries, et al., *A novel water-soluble fluorescent probe: Synthesis, luminescence and biological properties of the sodium salt of the 4-sulfonato-3,3',5,5'-tetramethyl-2,2'-pyrromethen-1,1'-BF₂complex*, RECL. TRAV. CHIM. PAYS-BAS 104, 288 (1985) incorporated herein by reference.

The products are generally soluble in organic solvents. Aqueous solubility can be obtained by adding appropriate water solubilization groups that includes sulfonates, carboxylates, ammonium and hydroxyl residues to the dyes. In most cases, the solid dyes are easily purified by techniques of chromatography and/or crystallization from a suitable solvent. Their chemical structures have been confirmed by nuclear magnetic resonance spectroscopy (Table 4).

TABLE 4

$^1$H-NMR SPECTRAL DATA OF REPRESENTATIVE NEW HETEROARYL-SUBSTITUTED DIPYRROMETHENEBORON DIFLUORIDE DYES

| COMPOUND | Chemical shift in ppm in CDCl$_3$ (300 MHz NMR) |
|---|---|
| 1 | 2.26(s, 3H, CH$_3$), 2.56(s, 3H, CH$_3$), 6.08(s, 1H, ArH), 6.31–6.37(m, 1H, ArH), 6.80(d, 1H, ArH), 6.87–6.90(m, 1H, ArH), 6.98(d, 1H, ArH), 7.00(s, 1H, ArCH=). |
| 2 | 6.37–6.41(m, 1H, ArH), 6.64(s, 1H, ArH), 6.92(d, 1H, ArH), 6.99–7.03(m, 1H, ArH), 7.08(d, 1H, ArH), 7.9–7.13(m, 1H, ArH), 7.21(s, 1H, ArCH=), 7.40–7.62(m, 8H, 8xArH), 7.96(d, 2H, 2xArH). |
| 3 | 2.29(s, 3H, CH$_3$), 2.60(s, 3H, CH$_3$), 6.20(s, 1H, ArH), 6.83(d, 1H, ArH), 6.95(d, 1H, ArH), 7.14(s, 1, ArCH=), 7.95(s, 1H, ArH), 8.03(s, 1H, ArH). |
| 4 | 6.80(s, 1H, ArH), 6.93(d, 1H, ArH), 7.07(d, 1H, ArH), 7.35(s, 1H, ArCH=), 7.46–761(m, 8H, 8xArH), 7.96(s, 1H, ArH), 8.00–8.07(m, 2H, ArH), 8.09(s, 1H, ArH). |
| 5 | 6.88(s, 1H, ArH), 7.08(d, 1H, ArH), 7.43(s, 1H, ArCH=), the other 15 aromatic protons are overlapped between 7.35 and 8.13. |
| 6 | 2.23(s, 6H, 2xCH$_3$), 2.62(s, 6H, 2xCH$_3$), 6.32(s, 2H, 2xArH), 7.43(s, 2H, 2xArH). |
| 7 | 2.14(s, 3H, CH$_3$), 2.48(s, 6H, 2xCH$_3$), the other 16 aromatic protons are overlapped between 6.50 and 7.65. |
| 8 | 2.27(s, 3H, CH$_3$), 2.61(s, 3H, CH$_3$), 6.14(s, 1H ArH), 6.72(d, 1H, ArH), 6.93(d, 1H, ArH), 7.08(s, 1H, ArCH=), 7.15(dd, 1H, ArH), 7.41(d, 1H, ArH), 8.06(d, 1H, ArH). |
| 9 | 6.74(s, 1H, ArH), 6.83(d, 1H, ArH), 7.06(d, 1H, ArH), 7.12–7.17(m, 1H, ArH), 7.30(s, 1H, ArCH=), 7.42–7.59(m, 9H, ArH), 7.99(d, 2H, ArH), 8.13(d, 1H, ArH). |
| 10 | 6.83(d, 2H, ArH), 7.03(d, 2H, ArH), 7.10(s, 1H, ArCH=), 7.17–7.22(m, 2H, ArH), 8.21(d, 2H, ArH). |
| 11 | 2.56(s, 3H, CH$_3$), 6.82(d, 2H, ArH), 7.22(d, 2H, ArH), 7.20–7.23(m, 2H, ArH), 7.46(d, 2H, ArH), 8.16(d, 2H, ArH). |

The spectral properties distinguish the heteroaryl dyes from the related alkyl-substituted 4,4-difluoro-4-bora-3a,4a-diaza-s-indacene dyes. As indicated by Table 2 and Table 3 below, the absorption and emission spectra of the heteroaryl dyes are all shifted to significantly longer wavelengths (typically > 540 nm in both cases) as compared to those of the parent alkyl-substituted 4,4-difluoro-4-bora-3a,4a-diaza-s-indacene dyes.

TABLE 2

PHYSICAL PROPERTIES OF REPRESENTATIVE NEW HETEROARYL-SUBSTITUTED DIPYRROMETHENEBORON DIFLUORIDE DYES

| COMPOUND | M.P. (°C.) | $\lambda^{Abs}_{max}$ (nm)* | $\lambda^{Em}_{max}$ (nm)* | $R_f$ | TLC Solvent |
|---|---|---|---|---|---|
| 1 | 180–181 | 585.6 | 595 | 0.57 | CHCl$_3$ |
| 2 | 209–210 | 614.8 | 638 | 0.56 | CHCl$_3$ |
| 3 | 236–238 | 546.4 | 556 | 0.47 | MeOH/CHCl$_3$ (5/95) |
| 4 | 223–225 | 584.4 | 603 | 0.55 | MeOH/CHCl$_3$ (5/95) |
| 5 | 245(dec) | 587.4 | 609 | 0.32 | CHCl$_3$ |
| 6 | 187–189 | 546.8 | 571 | 0.39 | CHCl$_3$ |
| 7 | 156–157 | 550.8 | 610 | 0.36 | CHCl$_3$ |
| 8 | 163–164 | 563.2 | 572 | 0.56 | CHCl$_3$ |
| 9 | 224–226 | 596.0 | 618 | 0.44 | EtOAc/Hexane (3/7) |
| 10 | 170–172 | 624.8 | 637 | 0.31 | EtOAc/Hexane (3/7) |
| 11 | 212–214 | 612.8 | 629 | 0.31 | EtOAc/Hexane (3/7) |

*The absorption and emission maxima of the representative compounds were measured in CHCl$_3$ except for Compound 6 for which the absorption and emission maxima were measured in MeOH.

Figure 4:
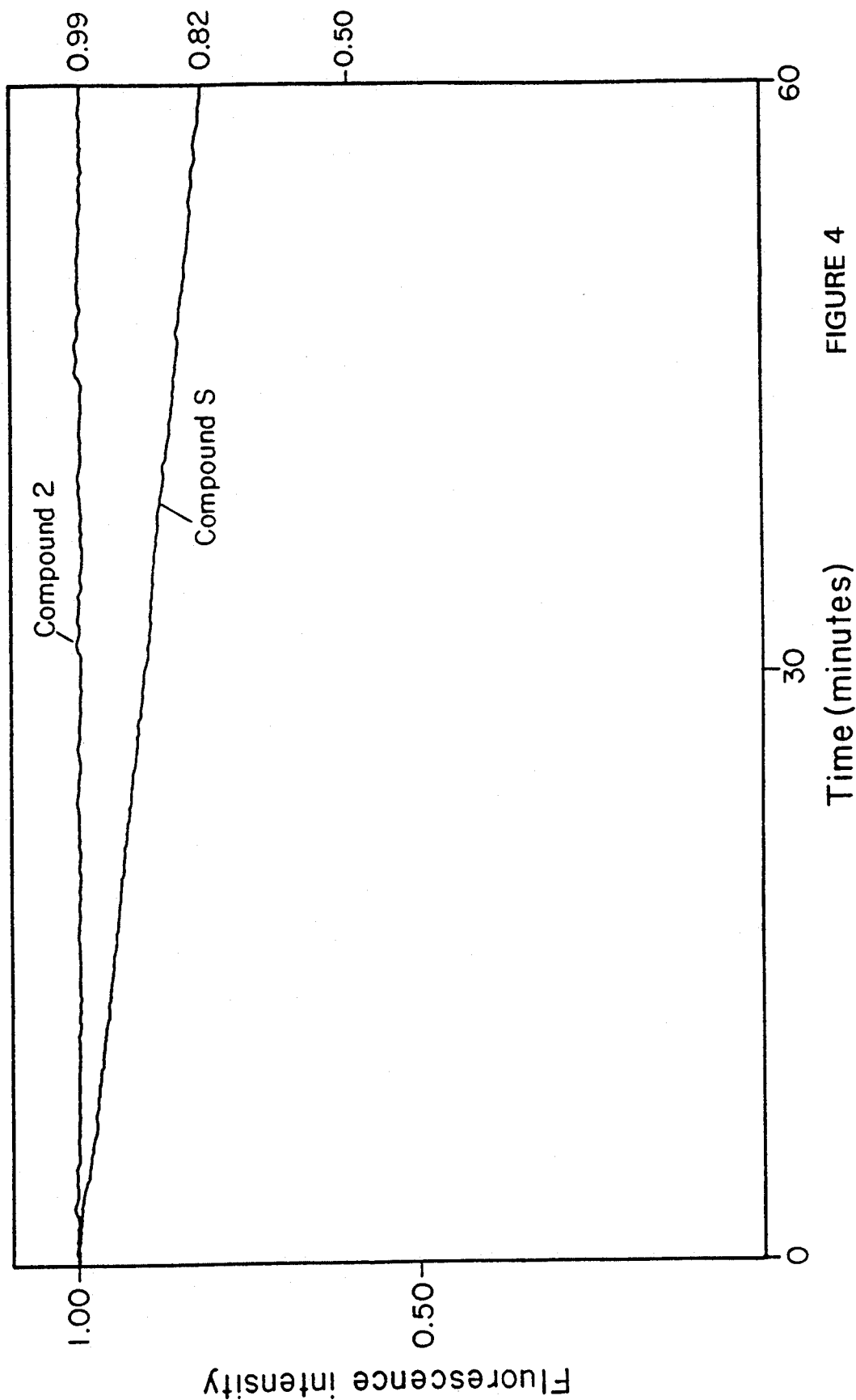
FIG. 4 is a graph showing the increased photostability of a selected heteroaryl dye in comparison with an alkyl-substituted dipyrrometheneboron difluoride dye, in $CH_3CN$ solution.

The heteroaryl dyes also demonstrate improved photostability (see Table 3, Example 14, and FIG. 4) relative to the alkyl-substituted 4,4-difluoro-4-bora-3a,4a-diaza-s-indacene dyes; with high extinction coefficients, generally greater than 70,000 cm$^{-1}$M$^{-1}$ (see Table 3).

TABLE 3

SPECTRAL PROPERTIES OF SELECTED HETEROARYL-SUBSTITUTED DIPYRROMETHENEBORON DIFLUORIDE DYES

| Compound | $\lambda^{Abs}_{max}$ (nm) | $\epsilon \times 10^{-3}$ (cm$^{-1}$M$^{-1}$) | $\lambda^{Em}_{max}$ (nm) | Quantum Yield ($\phi$) | Photostability§ |
|---|---|---|---|---|---|
| 1 | 585.6 | 104.1 | 595 | 0.67 | 0.83 |
| 2 | 614.6 | 83.4 | 638 | 0.37 | 0.99 |
| 3 | 546.6 | 79.3 | 556 | 1.00 | 0.95 |
| 4 | 584.6 | 74.5 | 603 | 0.74 | 0.97 |
| 8 | 563.4 | 75.6 | 572 | 1.00 | 0.96 |
| 10 | 624.2 | 75.5 | 637 | 0.50 | 0.98 |

TABLE 3-continued
SPECTRAL PROPERTIES OF SELECTED HETEROARYL-SUBSTITUTED DIPYRROMETHENEBORON DIFLUORIDE DYES

| Compound | $\lambda^{Ab}_{max}$ (nm) | $\epsilon \times 10^{-3}$ (cm$^{-1}$M$^{-1}$) | $\lambda^{Em}_{max}$ (nm) | Quantum Yield ($\phi$) | Photostability§ |
|---|---|---|---|---|---|
| S* | 506.4 | 89.8 | 515 | 1.00 | 0.82 |

*Compound S is presented as an example of alkyl-substituted dipyrromethenehoron difluoride dyes for comparison.

Absorption maxima ($\lambda^{Ab}_{max}$) and emission maxima ($\lambda^{Em}_{max}$) were measured in chloroform solution. Extinction coefficients ($\epsilon$) are shown in units of $10^3 \times$ cm$^{-1}$M$^{-1}$ at their absorption maxima in chloroform solution.

Fluorescence quantum yields ($\phi$) in methanol were measured relative to fluorescein in 0.1M NaOH ($\phi = 0.92$). Integrated fluorescence intensities were corrected for variation of solvent refractive index. The integrated fluorescence intensity was also corrected for variation of incident excitation light intensity with wavelength by recording spectra in ratio mode relative to a rhodamine B/ethylene glycol quantum counter solution. Ref.: J. N. Demas & G. A. Crosby. J. PHYS. CHEM., 75, 991-1024 (1971).

§Photostability data shows retention of emission intensity of dyes after continuous illumination at their excitation maxima for one hour in acetonitrile solution (see EXAMPLE 14).

Figure 2:
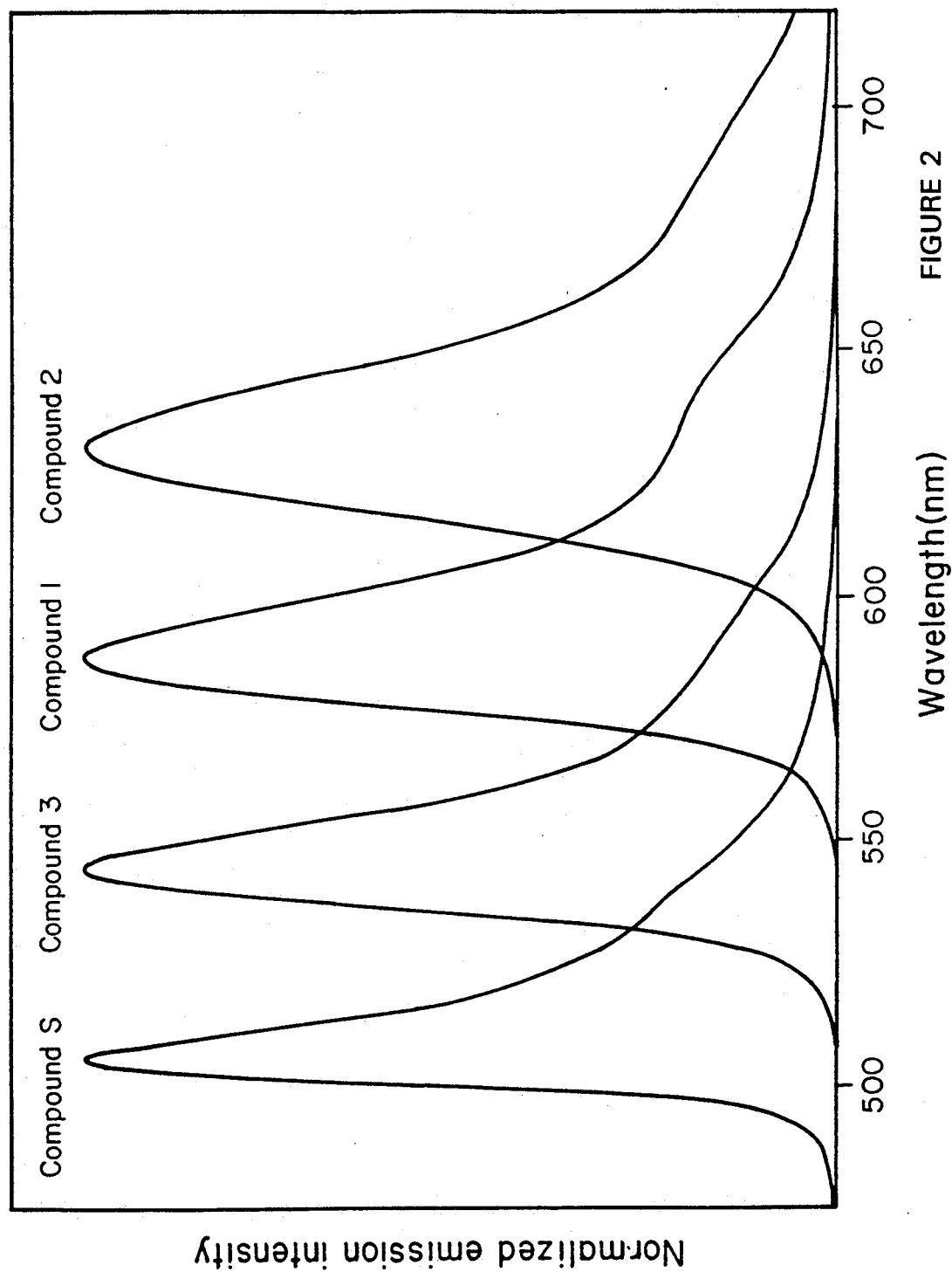
FIG. 2 is a graph of the relative spectral separations of selected examples of heteroaryl dyes in comparison with an alkyl-substituted dipyrrometheneboron difluoride dye, in methanol solution.
Figure 3:
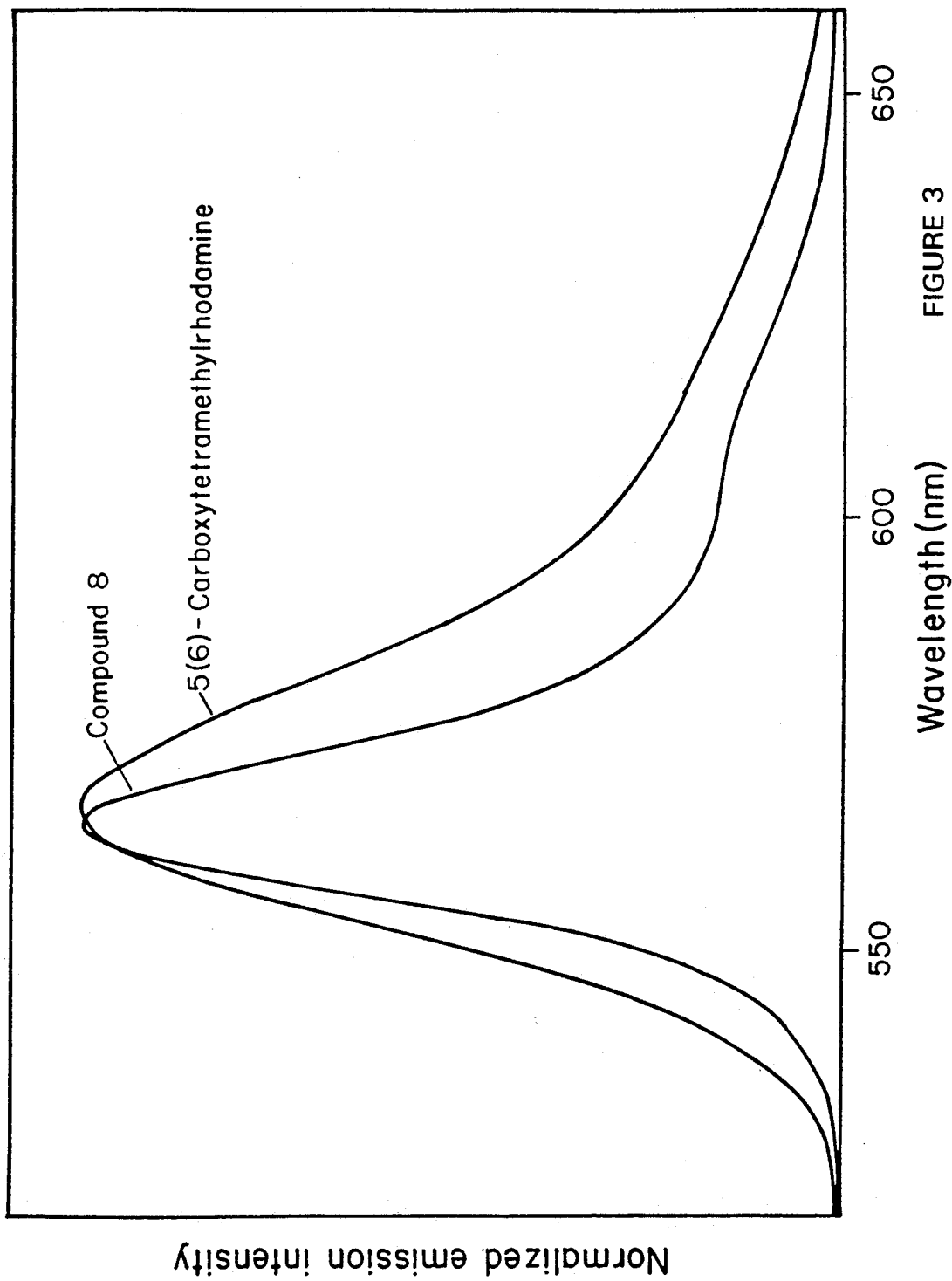
FIG. 3 is a graph showing the relatively narrow emission band width of a selected heteroaryl dye in comparison with another known dye emitting at the same wavelength (in methanol, excited at 540 nm).

Of further significance is the characteristic that the emission spectra of appropriate combinations of the dyes can be readily resolved (FIG. 2). This relatively high degree of spectral resolution is partly the result of the unusually narrow emission band width of the entire class of 4,4-difluoro-4-bora-3a,4a -diaza-s-indacene dyes relative to that of other important fluorophores that are in common use such as tetramethylrhodamine derivative (FIG. 3). Furthermore, unlike other long wavelength dyes such as the carbocyanines, the fluorescence of the heteroaryl-substituted 4,4-difluoro-4-bora-3a,4a-diaza-s-indacene dyes is usually not quenched in aqueous solution. This general insensitivity of the dye fluorescence to the environment for this class of dyes increases the utility of these dyes in their applications.

The following examples of the synthesis and characterization of the heteroaryl-substituted 4,4-difluoro-4-bora-3a,4a-diaza-s-indacene dyes and their characterization is intended to illustrate the generality of the invention and not to define or limit the scope of the invention.

EXAMPLE 1

4,4-Difluoro-5,7-dimethyl-3-(pyrrol-2-yl)-4-bora-3a,4a-diaza-s indacene

Compound 1

To a solution of 93 mg (0.76 mmol) of 3,5-dimethylpyrrole-2-carboxaldehyde and 100 mg (0.76 mmol) of 2,2'-bipyrrole in 15 mL of dichloromethane was added 75 μL (0.81 mmol) of phosphorus oxychloride. The reaction mixture was stirred at room temperature for 12 hours and was added 450 μL (3.23 mmol) of N,N-diisopropylethylamine, followed by addition of 400 μL (3.25 mmol) of boron trifluoride etherate. After the whole mixture was stirred at room temperature for 2 hours, it was washed with two 20 mL portions of water. The organic layer was separated, dried over anhydrous sodium sulfate and concentrated under reduced pressure to give a dark red solid. The crude product was purified by chromatography on silica gel with 30% chloroform in hexane as eluant to give 57 mg (27%) of a dark purple solid.

2,2'-Bipyrrole was prepared as described in H. Rapoport et al., J. AM. CHEM. SOC. 84,2178 (1962). 3,5-Dimethyl-2-pyrrolecarboxaldehyde was prepared from 2,4-dimethylpyrrole by the Vilsmeyer Haak formylation, according to R. M. Silverstein et al., ORG. SYNTH. COLL. Vol. IV, p. 831. 2,4-Dimethylpyrrole was prepared as described by A. Treibs et al., ANN. DER CHEMIE 739, 225 (1970).

EXAMPLE 2

4,4-Difluoro-5,7-diphenyl-3-(pyrrol-2-yl)-4-bora-3a,4a-diaza-s-indacene

Compound 2

This was prepared in the same manner as described in EXAMPLE 1 from 3,5-diphenylpyrrole-2-carboxaldehyde (90 mg, 0.36 mmol) and 2,2'-bipyrrole (50 mg, 0.37 mmol). The Compound 2 (49 mg, 33%) was obtained as a dark blue solid.

3,5-diphenylpyrrole-2-carboxaldehyde was prepared from 2,4-diphenylpyrrole by the Vilsmeyer Haak formylation. 2,4-Diphenylpyrrole was prepared as described in C. F. H. Allen et al., ORG. SYNTH. COLL. Vol. III, p. 33.

EXAMPLE 3

4,4-Difluoro-5,7-dimethyl-3-(oxazol-5-yl)-4-bora-3a,4a-diaza-s-indacene

Compound 3

To a solution of 30 mg. (0.31 mmol) of 2,4-dimethylpyrrole and 50 mg (0.31 mmol) of 5-(5-formylpyrrol-2-yl)oxazole in 1 mL of ethanol was added 50 μL of 48% hydrobromic acid while the reaction mixture was stirred vigorously in an ice bath. After stirring in an ice bath for 1 hour, the resulting orange precipitate was collected by filtration and dried under vacuum to give 78 mg of a crude dipyrromethene intermediate. This was suspended in 5 mL of dichloromethane and was added 200 μL (1.15 mmol) of N, N-diisopropylethylamine followed by addition of 140 μL (1.14 mmol) of boron trifluoride etherate. After the mixture was stirred at room temperature for 1 hour, it was washed with two 5 mL portions of water. The organic layer was separated, dried over anhydrous sodium sulfate and concentrated under reduced pressure to give a brown solid. The crude product was purified by chromatography on silica gel with chloroform as eluant to give 40 mg (45%) of the desired Compound 3 as an orange-red solid.

5-(Pyrrol-2-yl)oxazole and 5-(5-formylpyrrol-2-yl)oxazole needed for this synthesis were prepared as follows: To a solution of 3.91 g (0.02 mol) of tosylmethylisocyanide and 4.70 g (0.02 mol) of 1-benzenesulfonyl-2-formylpyrrole in 140 mL of methanol was added 1.38 g (0.01 mol) of potassium carbonate and the mixture was stirred at room temperature overnight. The resulting white precipitate was collected by filtration. To this precipitate were added 120 mL of methanol and 30 mL of 5N sodium hydroxide and the resulting suspension was heated under reflux for 20 minutes. After cooling down to room temperature, the reaction mixture was concentrated under reduced pressure to remove most of the methanol. To the resulting residue were added 200 mL of chloroform and 100 mL of water. After it was stirred at room temperature for 30 minutes, the organic layer was separated, dried over anhydrous sodium sulfate. The crude product was purified by chromatography on silica gel with chloroform as eluant to give 0.74 g (28%) of 5-(pyrrol-2-yl)oxazole as a white solid, m.p. 57°-58° C.; $^1$H-NMR (CDCl$_3$) δ 6.28-6.31 (m, 1H, ArH), 6.52-6.54 (m, 1H, ArH), 6.87-6.89 (m, 1H, ArH), 7.09 (s, 1H, ArH), 7.80 (s, 1H, ArH), 8.94 (bs, 1H, NH).

To an ice cooled 1 mL dimethylformamide was added 0.82 g (5.4 mmol) of phosphorus oxychloride while stirring under a nitrogen atmosphere. The mixture was stirred 20 minutes and then was added a solution of 0.60 g (4.5 mmol) of 5-(pyrrol-2-yl)oxazole in 15 mL of 1,2-dichloroethane while cooling in an ice bath. The reaction mixture was then heated under reflux for 20 minutes. After cooling to room temperature, 50 mL of chloroform was added followed by 60 mL of saturated aqueous sodium acetate. After heating under reflux for 20 minutes, the mixture was cooled to room temperature and the organic layer separated, washed with aqueous sodium carbonate and dried over anhydrous sodium sulfate. Following evaporation of the solvent at reduced pressure, the crude product was purified by column chromatography with chloroform elution to give 0.58 g (80%) of 5-(5-formylpyrrol-2-yl)oxazole as a white solid, m.p. 152°–153° C.; $^1$H-NMR (Acetone-d$_6$) δ 6.68 (d, 1H, ArH), 7.09 (d, 1H, ArH), 7.61 (S, 1H, ArH), 8,22 (s, 1H, ArH), 9.57 (s, 1H, CHO).

Also the Compound 3 (17 mg. 40%) was prepared in the same manner as described in EXAMPLE 1 from 3,5-dimethylpyrrole-2-carboxaldehyde (18 mg. 0.15 mmol) and 5-(pyrrol-2-yl)oxazole (20 mg. 0.15 mmol).

EXAMPLE 4

4,4-Difluoro-5,7-diphenyl-3-(oxazol-5-yl)-4-bora-3a,4a-diaza-s-indacene

Compound 4

This was prepared in the same manner as described in EXAMPLE 1 from 3,5-diphenylpyrrole-2-carboxaldehyde (36 mg. 0.15 mmol) and 5-(pyrrol-2-yl)oxazole (20 mg. 0.15 mmol). The Compound 4 (15 mg. 25%) was obtained as a dark purple solid.

EXAMPLE 5

4,4-Difluoro-3-(benzoxazol-2-yl)-5,7-diphenyl-4-bora-3a,4a-diaza-s-indacene

Compound 5

This was prepared in the same manner as described in EXAMPLE 1 from 3,5-diphenylpyrrole-2-carboxaldehyde (33 mg. 0.13 mmol) and 2-(pyrrol-2-yl)benzoxazole (25 mg. 0.12 mmol). The Compound 5 (7 mg. 11%) was obtained as a dark purple solid.

2-(Pyrrol-2-yl)benzoxazole was prepared as follows: A mixture of 5.55 g (0.05 mol) of pyrrole-2-carboxylic acid and 5.46 g (0.05 mol) of o-aminophenol and 3.09 g (0.05 mol) boric acid in 50 mL of xylene was heated under reflux for 3 days while removing water which was generated from reaction using a Dean-Stark trap. The cooled reaction mixture was diluted with 100 mL of ethyl acetate, washed with 150 mL of 5% sodium hydroxide solution and then with 150 mL of water. The separated organic layer was dried over anhydrous sodium sulfate. The resulting crude product was purified by column chromatography on silica gel with 20% hexane in chloroform as eluant. The desired product, 2-(pyrrol-2-yl)benzoxazole (4.75 g, 52%), was obtained as a white solid. m.p. 149°–150° C.; $^1$H NMR (CDCl$_3$) δ6.38–6.40 (m, 1H, ArH), 7.05–7.06 (m, 1H, ArH), 7.11–7.13 (m, 1H, ArH), 7.29–7.36 (m, 2H, 2xArH), 7.53–7.56 (m, 1H, ArH), 7.65–7.69 (m, 1H, ArH), 10.9 (bs, 1H, NH).

EXAMPLE 6

4,4-Difluoro-1,3,5,7-tetramethyl-8-(imidazol-2-yl)-4-bora-3a,4a-diaza-s-indacene

Compound 6

To a suspension of 25 mg (0.26 mmol) of 2-imidazolecarboxaldehyde and 50 mg (0.52 mmol) of 2,4-dimethylpyrrole in 5 mL of dichloromethane was added 50 μL of N,N-diisopropylethylamine and 250 μL of boron trifluoride etherate and the whole reaction mixture was stirred at room temperature overnight. It was washed with brine (2×5 mL), dried over anhydrous sodium sulfate and concentrated under reduced pressure. The resulting crude product was purified by silica gel column chromatography with 40% chloroform in hexane as eluant to give 7 mg (9%) of Compound 6 as an orange red solid.

EXAMPLE 7

4,4-Difluoro-3,5-[3-(2-methylbenzofuranyl)]-8-(2-acetoxyphenyl)-4-bora-3a,4a-diaza-s-indacene

Compound 7

To a solution of 50 mg (0.09 mmol) of 5,5'-bis[3-(2-methylbenzofuranyl)]-6-(2-acetoxyphenyl)-2,2'-dipyrromethene in 5 mL of dichloromethane was added 40 mg (0.18 mmol) of proton sponge and the mixture was stirred at room temperature for 10 minutes. It was then added 30 μL (0.24 mmol) of boron trifluoride etherate and the mixture was stirred at room temperature for two hours. The resulting precipitate was removed by filtration and the filtrate was concentrated under reduced pressure. The crude product was purified by silica gel column chromatography with 1/1 (hexane/chloroform) as eluant to give 21 mg (27%) of Compound 7 as a dark red solid.

The preparation of 5,5'-bis[3-(2-methylbenzofuranyl)]-6-(2-acetoxyphenyl)-2,2'-dipyrromethene was described in J. A. S. Cavaleiro et al., J. ORG. CHEM., 53, 5847 (1988).

EXAMPLE 8

4,4-Difluoro-5,7-dimethyl-3-(thien-2-yl)-4-bora-3a,4a,-diaza-s-indacene

Compound 8

This was prepared in the same manner as described in EXAMPLE 1 from 3,5-dimethylpyrrole-2-carboxaldehyde (77 mg., 0.63 mmol) and 2-(thien-2-yl)pyrrole (100 mg, 0.63 mmol). The Compound 8 (82 mg, 45%) was obtained as a dark purple solid.

The 2-(thien-2-yl)pyrrole needed for this synthesis was prepared as described in C. G. Kruse et al., HETEROCYCLES 26, 3141 (1987).

EXAMPLE 9

4,4-Difluoro-5,7,-diphenyl-3-(thien-2-yl)-4-bora-3a,4a-diaza-s-indacene, (Compound 9) and
4,4-Difluoro-3,5-di(thien-2-yl)-4-bora-3a,4a-diaza-s-indacene, (Compound 10)

These were prepared in the same manner as described in EXAMPLE 1 from 50 mg (0.2 mmol) of 3,5-diphenylpyrrole-2-carboxaldehyde and 35 mg (0.21 mmol) of 2-(thien-2-yl)pyrrole. After purification of the crude product by silica gel column chromatography with 30% ethyl acetate in hexane as eluant, Compound 9 (10 mg, 12%) and Compound 10 (8 mg, 11%) were obtained.

EXAMPLE 10

4,4-Difluoro-3,5-bis(thien-2-yl)-4-bora-3a,4a-diaza-s-indacene

Compound 11

To a solution of 100 mg (0.63 mmol) of 2-(thien-2-yl)pyrrole in 5 mL of dry dichloromethane was added 25 μL (0.35 mmol) of acetyl chloride and the solution was heated gently under reflux overnight. After cooling to room temperature, 250 μL (1.44 mmol) of N,N-diisopropylethylamine and 170 μL (1.38 mmol) of boron trifluoride etherate. After the mixture was stirred at room temperature for 1 hour, it was washed with two 5 mL portions of water. The organic layer was separated, dried over anhydrous sodium sulfate and concentrated under reduced pressure to give a dark blue solid. The crude product was purified by column chromatography on silica gel with chloroform/hexane (1/1) as eluant to give 34 mg (30%) of the desired Compound 11 as a dark purple solid.

EXAMPLE 11

2-(Pyrrol-2-yl)benzothiazole

A mixture of 5.55 g (50 mmol) of pyrrole-2-carboxylic acid, 6.26 g (50 mmol) of 2-aminothiophenol and 3.09 g (50 mmol) of boric acid in 250 mL of xylene was heated under reflux for 3 days while removing water which was generated from reaction using a Dean-Stark trap. the cooled reaction mixture was diluted with 200 mL of ethyl acetate, washed with 200 mL of 5% sodium hydroxide solution and then with 200 mL of water. The separated organic layer was dried over anhydrous sodium sulfate. The resulting crude product was purified by column chromatography on silica gel with 10% ethyl acetate in hexane as eluant. The desired product, 2-(pyrrol-2-yl)benzothiazole (1.40 g, 14%) was obtained as a pale yellow solid. m.p. 150°-151° C.; $^1$H-NMR (CDCl$_3$) 6.32-6.35 (m, 1H, ArH), 6.87-6.89 (m, 1H, ArH), 6.94-6.96 (m, 1H, ArH), 6.33 (t, 1H, ArH), 6.43 (t, 1H, ArH), 7.84 (d, 1H, ArH), 7.90 (d, 1H, ArH).

EXAMPLE 12

2-(Pyrrol-2-yl)benzimidazole

A mixture of 1.08 g (10 mmol) of o-phenylenediamine and 20 g of polyophosphate esters was heated gently at 80° C. and was added portionwise 1.11 g (10 mmol) of pyrrole-2-carboxylic acid. After the mixture was stirred at 100° C. for 30 minutes, it was poured into a saturated solution of sodium bicarbonate (500 mL) and stirred until polyphosphate esters was decomposed. It was then extracted with two 400 mL portions of ethyl acetate. the separated organic layer was dried over anhydrous sodium sulfate and concentrated under reduced pressure to give a crude product. After purification by column chromatography on silica gel with 30% ethyl acetate in hexane, the desired product, 2-(pyrrol-2-yl)benzimidazole (0.50 g, 25%) was obtained as a pale yellow solid, m.p. 250° C.; $^1$H-NMR (Acetone-d$_6$) 6.25-6.27 (m, 1H, ArH), 6.90-6.92 (m, 1H, ArH), 7.02-7.03 (m, 1H, ArH), 7.14-7.19 (m, 2H, 2xArH), 7.52 (bs, 2H, 2xArH).

EXAMPLE 13

SPECTRAL CHARACTERIZATION OF NEW HETEROARYL-SUBSTITUTED DIPYRROMETHENEBORON DIFLUORIDE DYES $^1$H-NMR spectra were measured using a Nicolet QE-300 MHz (General Electric) spectrometer for solutions in CDCl$_3$ unless otherwise stated with tetramethylsilane (TMS) as an internal standard. Chemical shifts are given in ppm from TMS and splitting patterns are designated as: s, singlet; d, doublet; t, triplet; m, multiplet. Results of spectral data for representative new heteroaryl-substituted dipyrrometheneboron difluoride dyes are given in Table 4.

Absorption measurements were obtained by dissolving the dye at a concentration of approximately $5 \times 10^{-6}$M in an appropriate solvent including methanol, chloroform, acetonitrile, acetone or hexanes using an IBM 9429 UV/Visible spectrophotometer. Extinction coefficients ($\epsilon$) of the dyes at their absorption maxima ($\lambda^{Abs}_{max}$) were determined by standard Beer's law calculations. Results of the spectral determination for representative heteroaryl dyes were tabulated in Table 2 and Table 3.

Fluorescence of new heteroaryl-substituted dipyrrometheneboron difluoride dyes was determined by dissolving the dye at a concentration above $1 \times 10^{-10}$M (optimum concentration ranges, $10^{-6} \sim 10^{-7}$M) in an appropriate solvent including but not limited to methanol, water, ethanol, acetonitrile, acetone, chloroform, toluene or hexane with a Perkin-Elmer Model 650-40 Fluorescence Spectrophotometer equipped with a Perkin-Elmer/Hitachi 057 X-Y Recorder. Results of the spectral determination for representative heteroaryl dyes are summarized in Table 2 and Table 3. Fluorescence could also be observed for the dyes in solution, or on thin layer chromatography (TLC) plates, by visual inspection with illumination by a suitable source that gives off light below 650 nm.

EXAMPLE 14

Photobleaching Studies

Photostability measurements of heteroaryl-substituted dipyrrometheneboron difluoride dyes were conducted in acetonitrile solution with continuous illumination by a 250 watt xenon arc lamp with 20 nm slit width at their absorption maxima. After one hour of continuous illumination while stirring at room temperature in a cuvette of fluorometer, emission intensity data was collected with 2.5 nm slit width at the emission maxima of individual samples. The results are listed in Table 3, together with that of the alkyl-substituted dipyrrometheneboron difluoride dye, Compound S, for comparison (also shown in FIG. 4). Concentrations of individual samples were prepared to have the same optical density for all of the dyes at the respective absorption maxima.

What is claimed is:

1. A compound of the structure:

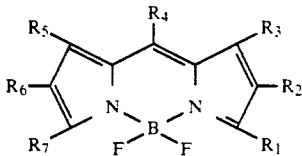

wherein at least one of substituents R₁–R₇ is a heteroaryl substituent attached to the remainder of the structure by a single covalent bond, and the remaining substituents are independently hydrogen, halogen, alkyl, cycloalkyl, arylalkyl, acyl, sulfo, nitro, carboxyl, hydroxyl, or amino;
the compound having an absorption maximum greater than about 540 nm in an organic solvent.

2. A compound, as claimed in claim 1, wherein at least one heteroaryl substituent is R₁, R₂, or R₃.

3. A compound, as claimed in claim 1, wherein at least one heteroaryl substituent is pyrrolyl, thienyl, or furanyl.

4. A compound, as claimed in claim 1, wherein one heteroaryl substituent is oxazolyl, isoxazolyl, oxadiazolyl, or imidazolyl.

5. A compound, as claimed in claim 1, wherein one heteroaryl substituent is benzoxazolyl, benzothiazolyl, or benzimidazolyl.

6. A compound, as claimed in claim 1, wherein one heteroaryl substituent is benzofuranyl or indolyl.

7. A compound, as claimed in claim 2, wherein R₁ is pyrrolyl; or alkyl-, aryl-, arylalkyl-, or heteroaryl-substituted pyrrolyl.

8. A compound, as claimed in claim 2, wherein R₁ is thienyl; or alkyl-, aryl-, arylalkyl-, or heteroaryl-substituted thienyl.

9. A compound, as claimed in claim 2, wherein R₁ and R₇, which may be the same or different, are pyrrolyl; or alkyl-, aryl-, arylalkyl-, or heteroaryl-substituted pyrrolyl.

10. A compound, as claimed in claim 2, wherein R₁ and R₇, which may be the same or different, are thienyl; or alkyl-, aryl-, arylalkyl-, or heteroaryl-substituted thienyl.

11. A compound, as claimed in claim 1, where one heteroaryl substituent is pyrrolyl, thienyl, furanyl, oxazolyl, isoxazolyl, oxadiazolyl, imidazolyl, benzoxazolyl, benzothiazolyl, benzimidazolyl, benzofuranyl, or indolyl, wherein said heteroaryl substituent is R₁, R₂, or R₃, the compound having an emission maximum greater than 550 nm.

12. A compound, as claimed in claim 1, having two heteroaryl substituents that are independently pyrrolyl, thienyl, furanyl, oxazolyl, isoxazolyl, oxadiazolyl, imidazolyl, benzoxazolyl, benzothiazolyl, benzimidazolyl, benzofuranyl, or indolyl, wherein one heteroaryl substituent is R₁, R₂, or R₃, the compound having an emission maximum greater than 550 nm.

13. A compound as claimed in claim 1 wherein R₁ is pyrrolyl; or methyl- or phenyl-substituted pyrrolyl, and the remaining substituents are independently hydrogen, methyl or phenyl.

14. A compound, as claimed in claim 1, wherein R₁ is thienyl; or methyl- or phenyl-substituted thienyl, and the remaining substituents are independently hydrogen, methyl or phenyl.

15. A compound, as claimed in claim 1, wherein R₁ and R₇, which may be the same or different, are pyrrolyl; or methyl- or phenyl-substituted pyrrolyl; or thienyl; or methyl- or phenyl-substituted thienyl.

16. A compound, as claimed in claim 15, wherein the remaining substituents are independently hydrogen, methyl or phenyl.

17. A compound of the structure:

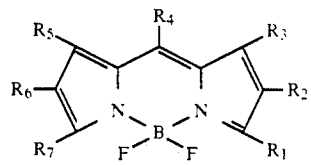

wherein at least one of substituents R₁, R₂, or R₃ is a heteroaryl substituent attached to the remainder of the structure by a single covalent bond, and the remaining substituents are independently hydrogen, halogen, alkyl, cycloalkyl, aryl, arylalkyl, acyl, sulfo, nitro, carboxyl, hydroxyl, or amino.

18. A compound, as claimed in claim 17, having two heteroaryl substituents that are independently pyrrolyl, thienyl, furanyl, oxazolyl, isoxazolyl, oxadiazolyl, imidazolyl, benzoxazolyl, benzothiazolyl, benzimidazolyl, benzofuranyl, or indolyl.

19. A compound, as claimed in claim 17, where one heteroaryl substituent is pyrrolyl, thienyl, furanyl, oxazolyl, isoxazolyl, oxadiazolyl, imidazolyl, benzoxazolyl, benzothiazolyl, benzimidazolyl, benzofuranyl, or indolyl.

20. A compound, as claimed in claim 17, wherein the remaining substituents are independently hydrogen, halogen, alkyl, acyl, sulfo, or nitro.

* * * * *

UNITED STATES PATENT AND TRADEMARK OFFICE
CERTIFICATE OF CORRECTION

PATENT NO. : 5,248,782
DATED : September 28, 1993
INVENTOR(S) : Haugland, et al.

It is certified that error appears in the above-indentified patent and that said Letters Patent is hereby corrected as shown below:

At col 15, line 13, "cycloalkyl, arylalkyl" should be --cycloalkyl, aryl, arylalkyl--.

Signed and Sealed this

Twenty-seventh Day of August, 1996

Attest:

BRUCE LEHMAN

Attesting Officer          Commissioner of Patents and Trademarks